United States Patent [19]
Johanson et al.

[11] Patent Number: 5,117,699
[45] Date of Patent: Jun. 2, 1992

[54] FLOW-NO-FLOW TESTER

[75] Inventors: Jerry R. Johanson, San Luis Obispo; Kerry D. Johanson, Atascadero; Brian D. Cox, San Luis Obispo, all of Calif.

[73] Assignee: JR Johanson, Inc., San Luis Obispo, Calif.

[21] Appl. No.: 610,530

[22] Filed: Nov. 8, 1990

[51] Int. Cl.⁵ ............................................. G01N 11/00
[52] U.S. Cl. ..................................................... 73/866
[58] Field of Search ............................ 73/866, 821, 823

[56] References Cited

U.S. PATENT DOCUMENTS

| | | | |
|---|---|---|---|
| 2,633,027 | 3/1953 | Bunnell | 73/866 |
| 3,890,830 | 6/1975 | Dyck | 73/825 |
| 4,719,809 | 1/1988 | Johanson et al. | 73/866 |

*Primary Examiner*—Robert Raevis
*Attorney, Agent, or Firm*—Daniel C. McKown

[57] ABSTRACT

An improved flow-no-flow tester has two major advantages over its predecessor. First, it eliminates the need to invert the test cell after the compaction phase, thereby eliminating the possibility that failure of the compacted sample will occur before the failure load-measuring portion of the test can be done. Second, the improved tester determines the compaction load by measuring the force exerted by the sample against an upper piston, while a compressive force is applied to the sample by a lower piston. This results in greater accuracy than was obtained in the predecessor wherein the compaction load was taken to be the force applied to the compressing piston and which was in error due to the forces of friction and particle binding on the piston as it advanced against the sample. In addition, the improved tester minimizes the potential of particle binding during the failure portion of the test. These advantages result from the structure of the tester, in which the test cell is closed at its bottom by a lower piston that is used for applying the compaction load and that is closed at its upper end by an upper piston against which the sample is pushed in the compaction phase and which is used subsequently for applying a downward failure load. The tester also permits the failure load to be applied at various rates so that the viscous properties of bulk solids and the pseudo strength of fine powders can be measured.

8 Claims, 3 Drawing Sheets

FLOW-NO-FLOW TESTER

BACKGROUND OF THE INVENTION

1. Field of the Invention

The present invention is in the field of bulk particulate solids, and more specifically relates to a testing apparatus and method for determining on the basis of bench-scale testing whether particulate material will flow under the action of gravity through an outlet in the bottom of a container, such as a hopper.

2. The Prior Art

Bulk solids in a divided state such as flour, sugar, ores, powders, dry chemicals, and coal are generally stored in silos that include a hopper at the lower end of the silo through which the bulk solids are to be discharged under the action of gravity. One of the problems of designing such containers is sizing the outlet so that the solids do not form an obstruction by arching across the outlet. The size of the outlet required to prevent arching depends on the physical properties of the bulk solids, specifically, the unconfined yield strength of the material, and the density of the material. The steepness of the walls of the hopper must also be considered.

The present invention is an outgrowth and improvement upon the apparatus shown and described in U.S. Pat. No. 4,719,809, issued Jan. 19, 1988 to Jerry R. Johanson and Kerry D. Johanson. The contents of that patent are hereby incorporated by reference into the present discussion as if reproduced herein verbatim. The patent is believed to be the most relevant prior art in relation to the present invention.

FIG. 1 is adapted from the aforementioned patent and shows a test apparatus described therein. The apparatus includes a mold ring 24' that rests upon a test cell 12'. The test cell 12' includes an inwardly-facing conical surface 14' and the test cell 12' is closed at its lower end by a conical surface 18'. The test cell is filled with a particulate material 32', which is compressed by a weighted disk 26'. After the material 32' has compacted, the mold ring 24' is removed and the material is scraped off even with the top of the test cell 12'.

Next, the entire filled test cell 12' is inverted and a failure load is applied downwardly to the plug 10'. As the failure load is gradually increased, a point is reached at which the material suddenly fails and falls out of the test cell. As discussed at greater length in the aforementioned U.S. Pat. No. 4,719,809, the size of outlet required to prevent arching can be calculated from the compaction load, the failure load, the density of the material, and the shape and dimensions of the outlet. That patent hints, at column 8, lines 21-28, that it might not be necessary to invert the test cell after the consolidation phase, but no apparatus is shown or described for bringing about this result.

In U.S. Pat. No. 3,890,830 issued Jun. 24, 1975 to Dyck, there is shown an apparatus for determining the compressibility and/or moisture content of particulate materials. Although there is a superficial resemblance to the apparatus of the present invention, upon closer study it will be seen that both the apparatus and the method of Dyck's tester are basically different from that of the present invention.

In U.S. Pat. No. 2,633,027 issued Mar. 31, 1953 to Bunnell, there is shown an apparatus and method for testing the flow characteristics of granular materials. The apparatus includes a cylindrical chamber which can selectively be opened and closed at its lower end, and a piston at its upper end for exerting compressive forces on the material. As will be seen below, both the structure and the operation of this apparatus is considerably different from that of the present invention.

SUMMARY OF THE INVENTION

It is an objective of the present invention to provide an improved flow-no-flow tester that is easier to use, compared with previous testers, and that yields more accurate results.

In using the tester described in U.S. Pat. No. 4,719,809 referred to above, it sometimes happened that when the test cell was inverted for application of the failure load, the compacted particulate material collapsed and fell out of the test cell before the test cell could be brought to its final position. Because of the evident nature of the problem, the accuracy of the results was not effected, but the test had to be repeated at some loss of time. The present invention solves this problem by eliminating the need to invert the test cell.

Less apparent, but nonetheless important is the improvement in the accuracy that is obtained with the apparatus of the present invention. In the apparatus of U.S. Pat. No. 4,719,809, the compaction force was taken to be the weight of the container 28' and ballast material 30' that rested on the sample 32' to compress it. Any friction or binding between the container and the cylindrical wall of the bore in which it extended had the effect of absorbing part of the applied force, with the result that the force actually brought to bear on the sample was less than indicated. In accordance with the present invention this problem is eliminated and the accuracy of the measurement is improved by measuring the force transmitted by the sample rather than the force applied to the sample.

A similar situation prevailed when the sample was so wet that it was necessary to enclose the sample in a membrane. Using the unimproved apparatus described in U.S. Pat. No. 4,719,809, any force that was required to deform the membrane was not measurable with that apparatus, which resulted the actual compaction force being less than the measured force, resulting in error. This problem is also overcome by the apparatus of the present invention in which the force transmitted by the sample is measured rather than the force applied to the membrane and sample.

In accordance with a preferred embodiment of the present invention these improvements are bought about by the structure of the apparatus in which a hollow test cell is closed off at its lower end by a lower piston that is used for applying an upward compaction force to the material, and is closed at its upper end by a concave upper piston which is used for resisting the applied compaction load, and later, for applying a downward failure load to the sample material. During the compaction phase, the compaction load is sensed by a compaction load cell that is actuated by the upper piston and which therefore measures the force transmitted by the particulate material.

After the particulate material has been compacted, the lower piston is retracted downwardly leaving the particulate material arched across the test cell. Next, a downward failure load is applied to the arched material by the upper piston, and this load is sensed by a load cell connected to the upper piston.

In addition to these improvements, the present invention includes several innovations. For example, there is provision in the preferred embodiment for selecting the rate at which the failure load is applied, and this feature extends the usefulness of the apparatus to viscous materials and to very finely divided materials containing a great deal of entrained air.

In the preferred embodiment, the portion of the test chamber within which the lower piston moves to compact the material is in the form of a collar that can be lowered out of the way after the material has been compacted, to accommodate any tendency of the material to expand upon failure, as happens when the material is highly elastic, such as particles of rubber.

The novel features which are believed to be characteristic of the invention, both as to organization and method of operation, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

DETAILED DESCRIPTION OF THE PREFERRED EMBODIDMENT

Figure 1:
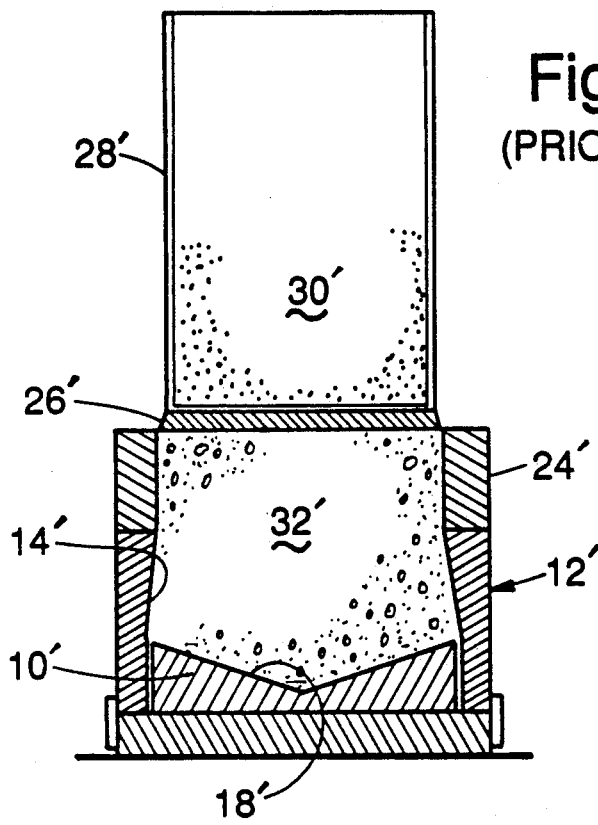
FIG. 1 is a side elevational view derived from U.S. Pat. No. 4,719,809 and showing a side elevational cross sectional view of a tester of the prior art.

Although the salient features of the present invention are independent of scale, in the preferred embodiment, the tester is designed to sit on a laboratory table or workbench, and the test cell 12 is several inches in diameter. The tester includes a base 11 to which a vertically-extending column 13 is affixed. A shelf 15 is supported above the base 11, and the test cell 12 sits on the shelf 15. An arm 17 extends from the column 13 above the shelf 15.

The test cell 12 includes an upper member 34 having an inwardly-facing conical surface 14 bounded above and below by an upper edge 38 and lower edge 36. The test cell 12 is further bounded by a lower member 24 having an inwardly-facing cylindrical surface 22 bounded above and below by the upper edge 30 and the lower edge 28, respectively, and defining a bore through which the lower piston 26 can travel. In the preferred embodiment, the lower member has the form of a collar that is removable from the upper member so as to provide a space below the inwardly-facing conical surface 14 to accommodate expansion of those materials that undergo expansion as they fail. In the preferred embodiment, raising and lowering of the lower member 24 is facilitated by the provision of radially-extending pins 27, 29 that are moved by the user within inclined slots, of which the slot 31 is typical, in the test cell wall.

Figure 3:
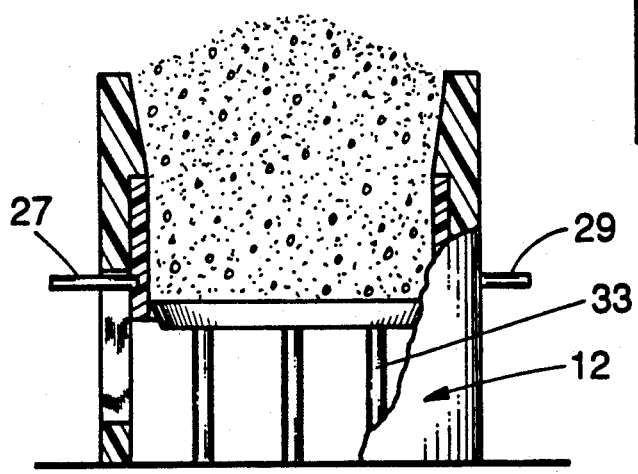
FIG. 3 is a side elevational view partly cut away and showing the test cell in a preferred embodiment.

The test cell 12 is closed at its bottom by the lower piston 26 which is driven upwards and downwards by the linear actuator 40 that consists of a motor 21 with a threaded shaft 23 that drives a stage 25 when the motor 21 is activated. In the preferred embodiment, the lower piston 26 is supported by three legs that are attached to it, of which the leg 33 is typical. These legs bear upon, but are not attached to, the upper end of the stage 25. This permits the lower piston to accompany the test cell when the latter is filled, as shown in FIG. 3.

Figure 2:
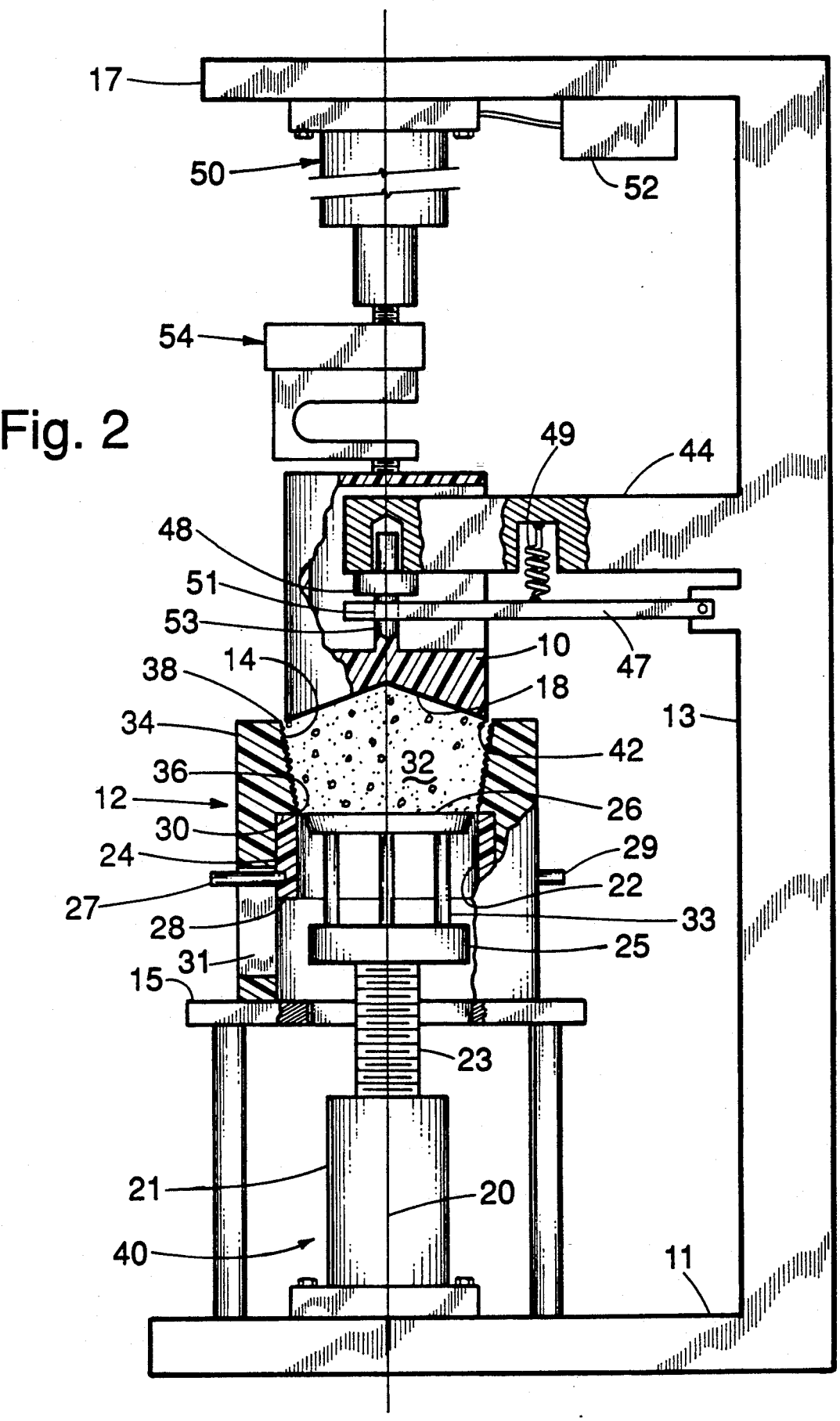
FIG. 2 is a side elevational view partly cut away and showing a preferred embodiment of the present invention.

The test cell 12 is closed at its top by the upper piston 10 which includes an inwardly-facing concave surface 18 that extends downward to a lower edge 42. The diameter of the concave surface 18 at its lower edge 42 is slightly less than the diameter of the concave surface 14 at its upper edge 38. The amount of vertical motion that the upper piston undergoes is extremely limited. As seen in FIG. 2, the upper piston restraint arm 44 limits upward travel of the upper piston 10 so that the lower edge 42 stops slightly above the upper edge 38 of the upper member of the test cell. The upper piston restraint 44 does not interfere with downward motion of the upper piston. As seen in FIG. 2, the arm 47 includes a clearance hole 51 through which the piston rod 53 moves without restraint, until at the lower end of its range of motion the compaction load cell 48 contacts a horizontally-extending arm 47 that is supported by the spring 49. Downward motion of the upper piston 10 is produced by the upper piston linear actuator 50 that includes a motor 51 and a speed controller 52 for adjusting the speed of the motor.

During compaction, the lower piston 26 moves upwardly, pushing the solid particulate material 32 against the upper piston 10, which is forced against the upper piston restraint 44. The compaction load is measured by the compaction load cell 48.

The upper piston 10 is driven downwardly only during the failure phase of the test after the lower piston has been moved downwardly below the lower edge 36. The linear actuator 50 drives the upper piston 10 downwards, and the failure load applied by the upper piston is sensed by the failure load cell 54.

Ordinarily, the failure load is only a few percent of the compaction load and therefore it may be advantageous to use separate load cells, such as the load cells 48 and 54 of FIG. 2, which operate in different force ranges. However, in an alternative embodiment a single load cell having an extended operating range and located in the place of the failure load cell 54 is used. When a single load cell is used, the upper piston restraint 44 should be removed.

The weight of the upper piston is supported by the failure load cell 54 and the upper piston linear actuator 50 so that its weight does not bear on the solid particulate material 32.

The lower piston actuator 40 and the upper piston actuator 50 as well as the test cell 12 are all aligned with the imaginary vertical axis 20.

In operation, the upper piston 10 is raised so that its lower edge 42 clears the upper edge 38 of the test cell, and the lower piston 26 is lowered. The test cell is slid laterally on the shelf 15 to a convenient location where it can be filled. After it has been filled as shown in FIG. 3 the test cell is returned to its position on the shelf 15 and on the axis 20. Thereafter, the upper piston is lowered until its lower edge 42 is below the upper edge 38 of the test cell.

The compaction phase is then initiated by driving the lower piston upwardly, compressing the solid particulate material 32. Ideally, at the end of the compaction phase, the lower piston will be approximately at the level of the upper edge 30 of the cylindrical surface 22. The compaction load is measured by the compaction load cell 48.

Next, the lower piston 26 is driven downwardly, and the lower member 24 of the test cell is lowered onto the shelf 15. This leaves the solid particulate material 32 in an arched configuration above the open bottom of the upper member 34. Thereafter, the upper piston linear actuator 50 is activated to drive the upper piston downwardly, and the force exerted by the upper piston on the solid particulate material 32 is sensed by the failure load cell 54. The reading of the failure load cell at the instant of failure is the failure load.

Figure 4:
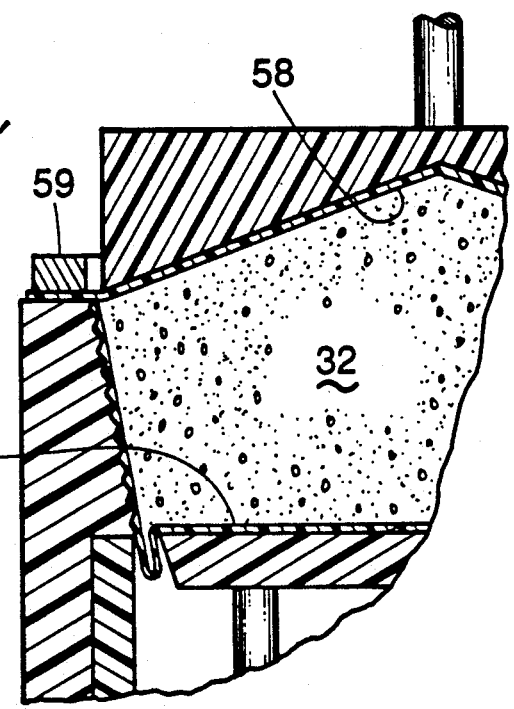
FIG. 4 is a diagram showing the use of membranes to contain a sample within the test cell.

FIG. 4 is a diagram showing the test cell removed from the tester and after it has been filled with a very moist material, which is prevented from flowing out of the test cell by the use of a lower membrane 56 and an upper membrane 58, the latter secured in place by a sealing ring 59.

In the preferred embodiment, the use of a motor driven linear actuator to fail the test sample allows testing at various strain rates, which gives insight to the viscous properties of the bulk solids.

The ability to alter the strain rate is also advantageous in measuring the pseudo strength of a fine powder created when the permeability of the powder is very low and it requires a significant time for air to enter the sample. This can be measured by running the failure motor fast. The maximum pseudo strength can be measured by sealing the test cell with a flexible membrane across its top and bottom during the failure portion of the test.

Compacting the solids from underneath while measuring the load transmitted to the upper piston 10 provides for the direct measurement of the load applied to the solids without concern for the friction or particle binding that might occur between the lower piston and the surface 22. This compaction method also provides the least potential for particle binding between the upper piston 10 and the converging portion 14 of the test cell. Both of these features are improvements over the device described in U.S. Pat. No. 4,719,809 and result in a significant improvement in accuracy.

The design of the present tester provides the possibility of measuring the failure characteristics of springback sensitive solids, such as plastic flakes, wood chips, and rubber chips, which have a tendency to deform elastically when the bulk mass is compacted. The elastic deformation causes the buildup of elastic restoring forces. These elastic restoring forces push against the container walls causing arching of an otherwise free-flowing, non-sticking granular solid. This condition can be tested for using the apparatus of the present invention and the following test procedure.

First, the sample is placed in the test cell with the lower piston 26 positioned at the height of the edge 36. The solids must be piled above the top of the test cell. Next, the cell is placed on the shelf 15 and secured there. Next, the solids are compacted from above using the upper piston linear actuator 50 to drive the upper piston 10 downward. It may be necessary to add additional solids and to again apply compression by means of the upper piston 10. The compaction is then held for the required time at rest. Next, the lower piston is moved downward and the test sample is failed by advancing the upper piston 10 while measuring the peak failure force by means of the failure load cell 54.

Figure 5:
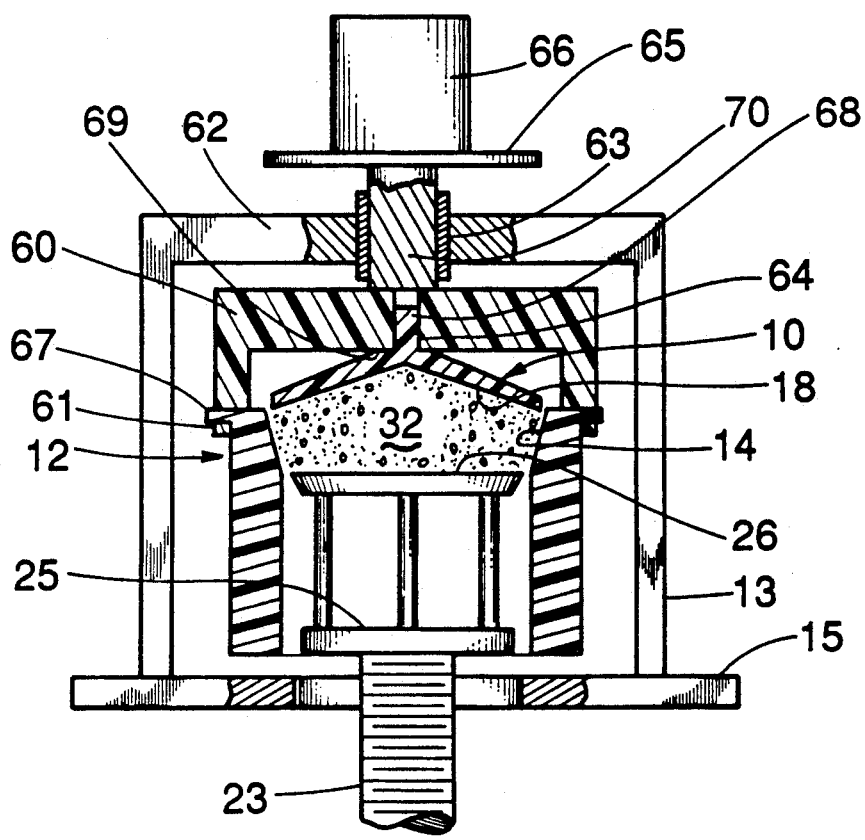
FIG. 5 is a side elevational view partly cut away and showing an alternative embodiment of the tester in its compaction mode; and, FIG. 6 is a side elevational view partly cut away and showing the alternative embodiment of FIG. 5 in its failure mode.
Figure 6:
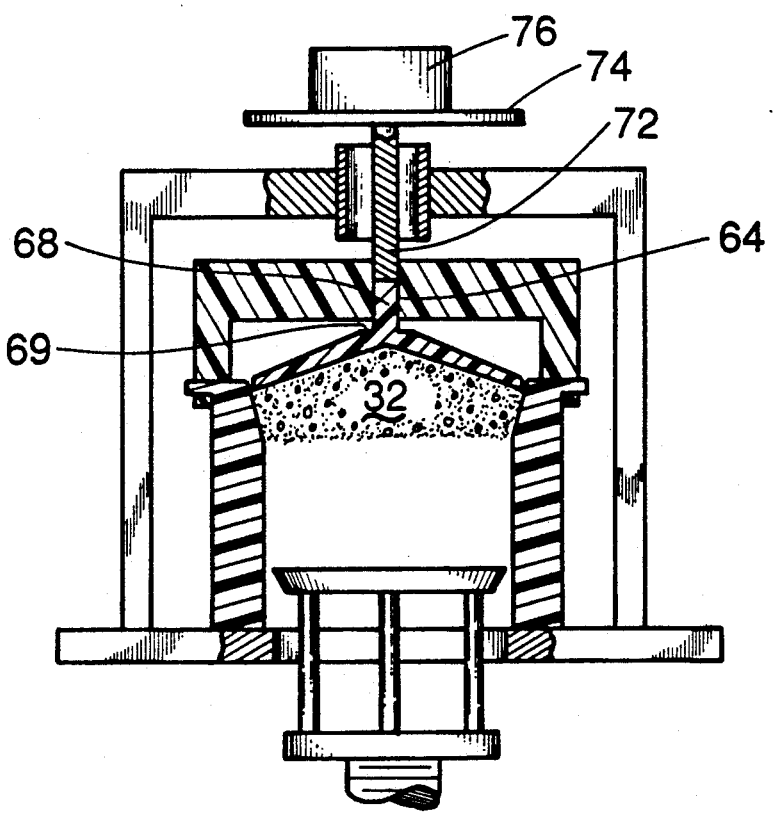

A related but somewhat different alternative embodiment is shown in FIGS. 5 and 6. The same reference numerals already used in connection with FIGS. 1-4 will be used, where applicable, to identify similar parts.

In the embodiment of FIG. 5, the threaded shaft 23 extends through the shelf 15 for moving the non-rotating stage 25 up and down. The stage 25 supports the lower piston 26 that is used to apply an upward force to the material 32 being tested.

The test cell 12 is provided with an outward flange 67 that extends, with interruptions, around the circumference of its upper edge. This interrupted flange is engaged by lugs, of which the lug 61 is typical on the removable cap 60. The upper piston 10 is provided with a pin 68 that is slidable within the guide 64 for the failure load. A shoulder 69 on the upper surface of the upper piston 10 restricts the upward motion of the pin 68 within the guide 64. From the shelf 15, vertical members 13 support a support frame 62 that, in turn, is rigidly affixed to the guide 63 for the compaction load. The compaction load 66 is supported on a weight stand 65. The weight stand 65 is affixed to a vertical shaft 70 that can slide freely vertically in the guide 63 for the compaction load.

In using the embodiment of FIG. 5, the cap 60 is removed and the material 32 is loaded into the test cell from the top, with the lower piston 26 partially lowered. Next, the upper piston 10 and the cap 60 are put into place, and the compaction process is started by advancing the lower piston 26 upwards. At some point, the compaction load is sufficiently great that the test cell 12 is lifted from the surface of the shelf 15. The lower end of the slidable shaft 70 rests on the upper surface of the cap 60, so that the total compaction load is the combined weight of the compaction load 66, the weight stand 65, the shaft 70, the cap 60, and the test cell 12. After a appropriate length of time which simulates the time during which the material in the full-scale bin sits before being unloaded, the lower piston is withdrawn downwardly, the weight of the compaction load 66 and of the weight stand 65 being supported by the support frame 62, and the weight of the cap 60 and the test cell 12 resting on the upper surface of the shelf 15. The lower piston is further lowered until it reaches the position shown in FIG. 6.

Thereafter, the compaction load 66 and the compaction load stand 65 including its shaft 70 are removed from the guide 63. Next, the shaft 72 of a failure load stand 74 is inserted in the guide 64 and a failure load 76 is gradually applied. The failure load 76 consists of a box into which sand or shot is gradually added until failure occurs. The lower end of the shaft 72 bears against the upper end of the pin 68 of the upper piston.

From this it can be seen that the embodiment of FIGS. 5 and 6 has the same advantages as the embodiment of FIG. 2. For example, it is not necessary to invert the test cell during the procedure, and also permits direct measurement of the load applied to the sample material without concern for the friction or particle binding that might occur between the lower piston and surrounding parts of the test cell.

Thus, there has been described an improved flow-no-flow tester that eliminates the need to invert the test cell and in which the compaction load is determined from the force transmitted by the test sample to the upper piston 10 rather than from the force applied to the sample by the lower piston 26, thereby significantly improving the accuracy by eliminating the effects of friction and particle binding between the lower piston 26 and the cylindrical portion 22 of the test cell.

The foregoing detailed description is illustrative of one embodiment of the invention, and it is to be understood that additional embodiments thereof will be obvious to those skilled in the art. The embodiments described herein together with those additional embodiments are considered to be within the scope of the invention.

What is claimed is:

1. A flow-no-flow tester that enables the testing to be carried out without having to invert a test cell containing a sample of a solid particulate material and without having to use an error-causing mold ring, said flow-no-flow tester comprising in combination:
   a) a test cell including an inwardly-facing cylindrical surface symmetrically disposed about an imaginary vertical axis, said cylindrical surface bounded vertically between a lower edge and an upper edge, said test cell further including an inwardly-facing conical surface symmetrically disposed about the imaginary vertical axis, having a lower edge immediately adjacent the upper edge of said cylindrical surface, and diverging upwardly to an upper edge of larger diameter than the lower edge;
   b) a lower piston fitting loosely into the bore defined by the inwardly-facing cylindrical surface of said test cell;
   c) lower piston drive means for raising and lowering said lower piston;
   d) an upper piston including an inwardly-facing concave surface symmetrically disposed about the imaginary vertical axis and diverging downwardly to a lower edge having a diameter approximately equal to but less than the diameter of the upper edge of the inwardly-facing conical surface of said test cell, the lower edge of said upper piston located adjacent the upper edge of the inwardly-facing conical surface of said test cell;
   e) upper piston restraint means for limiting the upward travel of said upper piston so that the lower edge of said upper piston is stopped by said upper piston restraint means slightly above the upper edge of the inwardly-facing conical surface of said test cell;
   f) compaction load measuring means for measuring the upward force exerted on said upper piston by the material in said test cell when the material is compressed by upward movement of said lower piston;
   g) downward force means for applying a downward force to said upper piston; and,
   h) failure load measuring means for measuring the downward force applied by said downward force means to said upper piston at the instant of failure.

2. The flow-no-flow tester of claim 1 wherein said test cell further includes a removable collar and wherein said inwardly-facing cylindrical surface of said test cell is part of said removable collar.

3. The flow-no-flow tester of claim 1 wherein said compaction load measuring means and said failure load measuring means are the same part.

4. The flow-no-flow tester of claim 1 wherein said downward force means further include a motor.

5. The flow-no-flow tester of claim 1 wherein said downward force means further include means for driving said upper piston downward at various speeds.

6. The flow-no-flow tester of claim 1 wherein said upper piston, said failure load measuring means, and said downward force means are connected so that said upper piston is supported by said failure load measuring means, whereby the failure load ca be less than the weight of said upper piston.

7. The flow-no-flow tester of claim 1 further including a pliable bag for containing the sample during testing.

8. A method for use in ascertaining whether a solid particulate material will flow under gravity through an outlet aperture of a hopper, said method comprising the steps of:
   a) loading a test cell with the solid particulate material, the test cell including a side wall, a movable lower piston, and a removable upper piston;
   b) inserting the test cell into an apparatus that includes a lower piston drive for pushing upwardly on the lower piston, and that includes an upper piston restraint that limits the upward movement of the upper piston;
   c) applying a compaction load by advancing the lower piston upwardly into the test cell to compact the solid particulate material against the upper piston;
   d) measuring the upward force exerted by the solid particulate material against the upper piston;
   e) lowering the lower piston;
   f) applying a downwardly-directed failure load to the upper piston; and,
   g) measuring the magnitude of the downwardly-directed failure load required to produce failure of the solid particulate material.

* * * * *